United States Patent [19]

Fox et al.

[11] Patent Number: 5,041,108

[45] Date of Patent: * Aug. 20, 1991

[54] METHOD FOR LASER TREATMENT OF BODY LUMENS

[75] Inventors: Kenneth R. Fox, Arlington; A. Arthur Coster, Alexandria, both of Va.

[73] Assignee: Pillco Limited Partnership, Arlington, Va.

[ * ] Notice: The portion of the term of this patent subsequent to Nov. 15, 2005 has been disclaimed.

[21] Appl. No.: 363,704

[22] Filed: Jun. 9, 1989

Related U.S. Application Data

[63] Continuation of Ser. No. 227,000, Jul. 29, 1988, Pat. No. 4,848,336, which is a continuation of Ser. No. 772,697, Sep. 5, 1985, Pat. No. 4,784,132, which is a continuation-in-part of Ser. No. 478,781, Mar. 25, 1983, Pat. No. 4,800,876, which is a continuation-in-part of Ser. No. 329,978, Dec. 11, 1981, abandoned, which is a continuation of Ser. No. 87,894, Oct. 24, 1979, abandoned, which is a continuation-in-part of Ser. No. 32,844, Apr. 24, 1979, abandoned.

[51] Int. Cl.⁵ .............................. A61B 17/36
[52] U.S. Cl. ............................ 606/7; 606/15
[58] Field of Search ............ 606/2.3, 7.8, 13–16; 128/395–398

[56] References Cited

U.S. PATENT DOCUMENTS

| | | | |
|---|---|---|---|
| 2,584,602 | 4/1951 | Greenburg | 128/4 |
| 3,136,310 | 6/1964 | Meltzer | 128/2 |
| 3,349,762 | 10/1967 | Kapany | 128/2 |
| 3,467,098 | 9/1969 | Ayers | 128/303.1 |
| 3,471,215 | 10/1969 | Snitzer | 350/96 |
| 3,538,919 | 11/1970 | Meyer | 128/398 |
| 3,556,085 | 1/1971 | Takahashi | 128/6 |
| 3,565,062 | 2/1971 | Kuris | 128/24 |
| 3,610,231 | 10/1971 | Takahashi | 128/6 |
| 3,659,613 | 5/1972 | Bredemeier | 128/395 |
| 3,674,013 | 7/1972 | Polanyi | 128/2 |
| 3,693,623 | 9/1972 | Harte et al. | 128/398 |
| 3,710,798 | 1/1973 | Bredemeier | 128/303.1 |
| 3,769,963 | 11/1973 | Goldman et al. | 128/395 |
| 3,794,040 | 2/1974 | Balamuth | 128/303.1 |
| 3,796,220 | 3/1974 | Bredemeier | 128/303.1 |

(List continued on next page.)

FOREIGN PATENT DOCUMENTS

| | | |
|---|---|---|
| 0144764 | 6/1985 | European Pat. Off. . |
| 1900017 | 8/1970 | Fed. Rep. of Germany . |
| 2062951 | 9/1971 | Fed. Rep. of Germany . |
| 2511248 | 12/1975 | Fed. Rep. of Germany . |
| 2640406 | 3/1978 | Fed. Rep. of Germany . |
| 2740969 | 3/1979 | Fed. Rep. of Germany . |
| 2368931 | 10/1976 | France . |
| WO8404879 | 12/1984 | PCT Int'l Appl. . |
| WO8500010 | 1/1985 | PCT Int'l Appl. . |
| WO8502532 | 6/1985 | PCT Int'l Appl. . |

OTHER PUBLICATIONS

Mulvaney et al., "The Laser Beam in Urology," J. of Urol., vol. 99, pp. 112-115 (Jan. 1968).

(List continued on next page.)

Primary Examiner—Max Hindenburg
Attorney, Agent, or Firm—Wigman & Cohen

[57] ABSTRACT

A laser microsurgical method and apparatus are disclosed for safely treating occluded body lumens with laser energy. The disclosed method involves the use of pulsed laser energy from an argon-ion laser to destroy the tissue of luminal occlusions, such as atheromatous plaque and the like, with substantially no thermal necrosis of the surrounding tissue. A flexible catheter and associated laser microsurgical system is also disclosed which provides for aiming of the fibers to transmit the laser beam at the distal end of the catheter and rotational positioning of the catheter to permit coverage of virtually the entire cross-sectional area of the lumen. A lens system at the distal end of each laser fiber minimizes beam divergence and directs the beam toward the central axis of the catheter. A further embodiment of the catheter of the invention provides an array of laser fibers which are optically scanned with laser energy to cover the cross-sectional area of the lumen. The system is designed to minimize the possibility of damage to or perforation of the surrounding tissue of the lumen.

6 Claims, 4 Drawing Sheets

U.S. PATENT DOCUMENTS

| | | | |
|---|---|---|---|
| 3,804,095 | 4/1974 | Bredemeier | 128/303.1 |
| 3,821,510 | 6/1974 | Muncheryan | 128/395 |
| 3,843,865 | 10/1974 | Nath | 219/121 L |
| 3,858,577 | 1/1975 | Bass et al. | 128/398 |
| 3,858,586 | 1/1975 | Lessen | 128/303.1 |
| 3,866,599 | 2/1975 | Johnson | 128/2 |
| 3,884,236 | 5/1975 | Krasnov | 128/303.1 |
| 3,897,775 | 8/1975 | Furihata | 128/6 |
| 3,906,953 | 9/1975 | Wallace et al. | 128/303.1 |
| 3,913,582 | 10/1975 | Sharon | 128/303.1 |
| 3,914,013 | 10/1975 | Rosenberg | 128/397 |
| 4,040,413 | 8/1977 | Ohshiro | 128/6 |
| 4,069,823 | 1/1978 | Isakov et al. | 128/303.1 |
| 4,072,147 | 2/1978 | Hett | 128/6 |
| 4,074,719 | 2/1978 | Semm | 128/303.1 |
| 4,091,814 | 5/1978 | Togo | 128/303.1 |
| 4,120,293 | 10/1978 | Muckerheide | 128/2 |
| 4,123,143 | 10/1978 | Yachin et al. | 350/171 |
| 4,141,362 | 2/1979 | Wurster | 128/395 |
| 4,141,364 | 2/1979 | Schultze | 128/4 |
| 4,146,019 | 3/1979 | Bass et al. | 128/6 |
| 4,170,997 | 10/1979 | Pinnow et al. | 128/395 |
| 4,204,528 | 5/1980 | Termanini | 128/6 |
| 4,207,874 | 6/1980 | Choy | 128/6 |
| 4,224,929 | 9/1980 | Furihata | 128/6 |
| 4,245,624 | 1/1981 | Komiya | 128/4 |
| 4,266,548 | 5/1981 | Davi | 128/303.1 |
| 4,273,109 | 6/1981 | Enderby | 128/6 |
| 4,309,998 | 1/1982 | Aron nee Rosa et al. | 128/395 |
| 4,418,688 | 12/1983 | Loeb | 128/6 |
| 4,576,435 | 3/1986 | Nishioka | 128/6 |
| 4,588,294 | 5/1986 | Siegmund | 128/634 |
| 4,686,979 | 8/1987 | Gruen et al. | 128/303.1 |
| 4,784,132 | 11/1988 | Fox et al. | 606/15 |
| 4,784,135 | 11/1988 | Blum et al. | 128/395 |
| 4,800,876 | 1/1989 | Fox et al. | 606/7 |

OTHER PUBLICATIONS

Schmidt-Kloiber, Aktuelle Nephrologie, Issue No. 1, pp. 117–147 (Feb. 1978) (w/English translation).

Fair, "In Viro Destruction of Urinary Calculi by Laser-Induced Stress Waves," Medical Instrumentation, vol. 12, pp. 100–105 (Mar.–Apr. 1978).

Tanahashi et al., "Disintegration of Urinary Calculi by Laser Beam: Drilling Experiment in Extracted Urinary Stones", Tohoku J. Exp. Med., vol. 128, pp. 189–196 (Jan. 1979).

Tanashi et al., "The Use of Laser Beam in Urology," Japan J. Urol., 70:1 (Jan. 1979) 2/English translation.

Tanahashi et al., "Transurethral Disintegration of Urinary Calculi by the Use of Laser Beams," Urology, pp. 10-30 to 10-33 (Jan. 1982).

Orii et al., "Choledocholithotomy by Yag Laser with a Choledochofiberscope: Case Reports of Two Patients," Surgery, vol. 90, No. 1, pp. 120–122 (Jul. 1981).

Orii et al., "Lithotomy of Intrahepatic and Choledochal Stones with Yag Laser," Surgery, Gynecology & Obstetrics, vol. 156 (Apr. 1983).

"Hypodermic Fiberscope," Max Epstein, Application of Optical Instrumentation in Medicine, 2nd Seminar, Chicago, IL (Nov. 29–30, 1973), pp. 113–116.

Limbectomies, Keratectomies and Keratostomies Performed With A Rapid Pulsed Carbon Dioxide Laser, Beckman et al., American Journal of Ophthalmogy, vol. 71, No. 6, pp. 1277–1283, Jun. 1981.

Pulsed Laser Iridotomy Apparatus, The Johns Hopkins University, Applied Physics Laboratory, Fraser et al., pub. date unknown but believed to be before 5/8/80.

American Heart Journal, Laser-Dissolution Of Coronary Atherosclerotic Obstruction, Dec. 1981, Garrett Lee et al., pp. 1074–1075.

Optics and Laser Technology, Fibre Bundle Scanner For Laser Photocoagulation Treatment, Feb. 1982, Fujii et al., pp. 39–40.

Applied Optics, Multispot Laser Photocoagulation System Using A Fiber Bundle Scanner, vol. 21, No. 19, Oct. 1982, Fujii et al., pp. 3437–3442.

American Heart Journal, Feasibility of Intravascular Laser Irradiation For In Vivo Visualization and Therapy of Cardiocirculatory Diseases, Jun. 1982, Lee et al., p. 1076.

The American Journal of Cardiology, Effects of Carbon Dioxide, Nd-Yag, and Argon Laser Radiation On Coronary Atheromatous Plaques, Dec. 1982, Abela et al., pp. 1199–1025.

The American Journal of Cardiology, Laser Coronary Angioplasty: Experience With 9 Cadaver Hearts, Dec. 1982, Choy et al., pp. 1209–1211.

The American Journal of Cardiology, Transluminal Laser Catheter Angioplasty, Dec. 1982, Choy et al., pp. 1206–1208.

(List continued on next page.)

OTHER PUBLICATIONS

L.I.A., vol. 32 ICALEO (1982), Interactions Between Material Processing and Surgery, Myron Wolbarsht, pp. 1–5.

Cardiology Times, 1983, Transluminal Laser Coronary Angioplasty Is Under Evaluation.

Science, Selective Photothermolysis: Precise Microsurgery By Selective Absorption of Pulsed Radiation, Apr. 1983, pp. 524–527.

Lasers in Surgery & Medicine, Far-Ultraviolet Laser Ablation of Atherosclerotic Lesions, Linsker et al., 1984, pp. 201–206.

Journal of Medical Engineering & Technology, Recanalization Of Arteries By Laser Radiation, Gillen et al., 1984, pp. 215–217.

Applied Optics, Argon Laser Disintegration Of Thrombus and Atherosclerotic Plaque, Kaminow et al., 1984, pp. 1301–1302.

Clin. Cardio., Human Coronary Laser Recanalization, Choy et al., 1984, pp. 377–381.

Laser Focus/Electro-Optics, Excimer Lasers Offer Promise In Surgical Applications, 1985, Muller et al., pp. 70–81.

American Journal of Cardiology, Reduction Of Laser-Induced Pathologic Tissue Injury Using Pulsed Energy Delivery, Deckelbaum et al., 1985, pp. 662–667.

PCT International Search Report, 11/25/86.

Partial European Search Report, EP 86 11 2166, 12/12/86.

Communication Pursuant to Article 96(2) and Rule 51(2), EPC, Nov. 3, 1988.

METHOD FOR LASER TREATMENT OF BODY LUMENS

CROSS REFERENCE TO RELATED APPLICATIONS

This application is a continuation of U.S. patent application Ser. No. 227,000 filed July 29, 1988, now U.S. Pat. No. 4,848,336, which is a continuation of U.S. patent application Ser. No. 772,697, filed Sept. 5, 1985, now U.S. Pat. No. 4,784,132, which is a continuation-in-part of U.S. patent application Ser. No. 478,781, filed Mar. 25, 1983, now U.S. Pat. No. 4,800,876 which is a continuation-in-part of U.S. patent application Ser. No. 329,978, filed Dec. 11, 1981, now abandoned, which is a continuation of U.S. patent application Ser. No. 087,894, filed Oct. 24, 1979, now abandoned, which is a continuation-in-part of U.S. patent application Ser. No. 032,844, filed Apr. 24, 1979, now abandoned.

BACKGROUND OF THE INVENTION

The present invention relates to a method of and apparatus for the laser treatment of occluded body lumens of mammals, especially humans, and more particularly to the intraluminal use of laser energy to perforate and/or remove luminal occlusions, such as thrombi and/or atherosclerotic placques in the cardiovascular system.

Cardiovascular disease is a major cause of death and morbidity and manifests a grave concern to both the scientific community and the lay public. Arteriosclerotic cardiovascular pathophysiology is a complex of diseases which affects many blood vessels in the body, the decreased lumen diameter causing tissue ischemia. Other very common diseases, such as diabetes mellitus, enhance the occlusion of important blood vessels and ischemia of the organs they supply. Those diseases, aggravated by such other common abnormalities as hypertension, and other vascular diseases and cardiovascular diseases, account for cerebrovascular accidents, myocardial infarctions, and other devastating illnesses, including loss of life and limb. Unfortunate individuals affected with arteriosclerotic cardiovascular disease and the related vasculopathies often manifest disease in coronary, carotid and cerebral arteries, in popliteal, tibial and dorsalis pedis arteries of the lower extremities and in other vessels. Those individuals, apart from having a shortened life expectancy, and suffering from sudden death, frequently also suffer from other debilitating problems including angina, shortness of breath and restricted activity, claudication or restricted use of the lower extremities, sometimes with loss of those extremities from disease, and loss of functions of movement, speech, cerebral interpretation and cognitive abilities.

Historically, there are few effective means for preventing some of the foregoing disastrous medical problems. Patients with certain types of coronary insufficiencies documented by certain coronary angiographic findings may be helped symptomatically by coronary artery bypass operations. Other patients sometimes may be benefited by other types of arterial surgery, for example, various bypass operations, or endarterectomies, which surgically attempt recanalization of certain occluded blood vessels or other operations. Those are generally patients with severe disease, but yet who meet certain diagnostic criteria and who are healthy enough to undergo what amounts to major surgery with relatively high morbidity and mortality rates. The cost is immense for many of these operations and incumbent hospitalization, including expensive special equipment which is required, and special training which is necessary for a team to operate the special surgical equipment. For example, it is estimated that a single coronary bypass operation may cost a patient over $50,000 including the hospitalization fees, and surgical fees. Availability of this special type of surgery for vascular problems is limited. Long term efficacy of coronary bypass surgery is as yet unknown, and the appropriate diagnostic and surgical criteria remain controversial. Because of the severity of the morphology and nature of the disease, for many patients treatment has been unavailable and has been beyond the current scope of surgical intervention. For example, many patients lose extremities or their lives by virtue of having these inoperable conditions.

In a different context, problems of lumens of the body, particularly small lumens, are complicated by occlusive diseases of other types. As an example in the nervous system, the Aqueduct of Sylvius, in the ventricular system of the brain, may be blocked in a child born with congenital hydrocephalus. This condition necessitates a complicated and often unsuccessful corrective neurosurgical procedure known as shunting. Considering the genito-urinary system, for example, fallopian tubes may become occluded by inflammatory or other disease processes. This may cause infertility and is a common problem. There is no effective treatment for this problem at this point in time, and this has stimulated interest in the "test tube baby" controversy.

One suggested solution to the problem of atherosclerotic obstructions is a non-operative technique to improve coronary blood flow known as percutaneous transluminal coronary angioplasty (PTCA). Generally, PTCA involves introducing a balloon catheter into the femoral artery or by brachial cutdown and fluoroscopic positioning at the appropriate coronary ostium. Pressure monitoring is also used to aid in positioning the balloon tip of the catheter at the stenosis. The balloon is inflated for 3-5 seconds to mechanically enlarge the stenosis and is then deflated for measurement of distal coronary pressure. The cycle may be repeated several times until a satisfactory decrease in pressure gradient is achieved.

Although the PTCA technique is sometimes effective to improve coronary blood flow, there are complications which must be weighed before undertaking the procedure. Such complications which may occur include arterial spasms, myocardial infarction, thrombotic occlusion, embolization and dissection, or frank perforation of the vessel wall.

It has also been suggested that cardiovascular occlusions, as well as occlusions in other body lumens, might be vaporized by means of continuous wave (CW) laser energy. U.S. Pat. No. 4,207,874 to Choy, for example, discloses a flexible conduit which accommodates a fiberoptic bundle divided into light source, viewing and laser bundle portions. The flexible conduit is introduced into a vein or other body lumen and advanced until it contacts an obstruction such as a thrombus. A laser apparatus optically associated with the laser fiber bundle is then activated so that the laser energy vaporizes the obstruction, the remaining particles of which are then removed by suction.

Other flexible laser endoscopes for use in the therapeutic laser treatment of body lumens are disclosed in U.S. Pat. Nos. 4,072,147; 4,146,019; 4,170,997; and German Offenlegungsschrift No. 2,640,406. Such intraluminal laser devices typically are said to function by thermal vaporization and/or coagulation of the luminal obstruction mass.

One of the most serious risks inherent in the intraluminal use of laser radiation, especially in coronary or cerebral blood vessels, is the possibility of perforation of or thermal damage to the vessel walls and surrounding tissue. Accordingly, intravascular recanalization of occluded blood vessels is still an experimental procedure.

Recently, investigators have reported the use of continuous wave (CW) argon, neodymium-YAG and carbon dioxide laser sources to successfully vaporize, coagulate and penetrate atherosclerotic placque in animals and in sections of coronary arteries taken from human cadavers. However, the investigators also report perforation of the vessel walls in many cases, particularly at laser energy levels which have been increased to a level sufficient to effect vaporization of the placque.

Such laser energy levels are appropriately characterized as the "thermal" mode of laser operation which involves causing damage to tissue by virtue of heat accumulation in the tissue impinged by the laser radiation. Excessive heat accumulation causes thermal degradation or thermal necrosis. In other words, the temperature of the tissue rises, tissue proteins are denatured and ultimately the tissue is coagulated and "evaporated" or "vaporized." While the laser thermal energy mode is effective in coagulating and vaporizing many tissues, including the tissues forming atherosclerotic placques and stenoses, its use heretofore in occluded coronary and cerebral blood vessels, for example, is not sufficiently safe and controllable. Consequently, the problem of inadvertent damage to or destruction of surrounding vessel tissue has been a major obstacle in the development of an acceptable microsurgical technique for laser angioplasty in the human vascular system.

Apart from the risk of using continuous wave (CW) laser energy in the human vascular system, the prior art intraluminal laser devices lack effective mechanisms for "aiming" the laser beam to minimize the possibility of inadvertent damage to the vessel walls and to maximize the exposure of a large area of the occlusion, e.g., the atherosclerotic placque, to the laser energy.

SUMMARY AND OBJECTS OF THE INVENTION

In view of the foregoing limitations and shortcomings of the prior art intraluminal laser devices, as well as other disadvantages not specifically mentioned above, it should be apparent that there still exists a need in the art for a laser microsurgical apparatus for use in coronary angioplasty which is capable of effecting recanalization of occluded coronary and cerebral blood vessels at minimum risk of perforation or thermal necrosis of the vessel walls. It is, therefore, a primary objective of this invention to fulfill that need by providing a novel coronary arterial catheter and associated laser microsurgical system and a method of using the same whereby the laser energy radiated within the cardiovascular system is carefully controlled and aimed in such a way as to effectively destroy or penetrate atherosclerotic placque, yet minimize the risk of vascular perforation or thermal necrosis of the surrounding tissue.

More particularly, it is an object of the present invention to provide an effective method of delivering laser energy in a safe, substantially non-heat conducting or conduction-free mode by controlling the pulse width or duration, pulse repetition rate, and duty cycle of the laser energy within predetermined ranges and by using optical switching to sequentially direct the laser energy at selected target areas.

It is another object of the present invention to provide a flexible catheter adapted to be inserted into a body lumen, such as an obstructed coronary artery, said catheter having one or more quartz glass laser fibers which can be "aimed" at a particular target within a target area comprising substantially the entire cross-sectional area of the body lumen.

Yet another object of the invention is to provide a laser microsurgical system connected to the proximal end of a flexible angiographic catheter for controlling the positioning, illumination, visualization, firing and analysis functions of the system.

Still another object of the invention is to provide a flexible angiographic catheter for use in occluded blood vessels in combination with laser microsurgical apparatus, said catheter having one or more laser fibers, each of which is provided with a lens system which minimizes divergence of the laser beam and prismatically cants the laser beam toward the center of the blood vessel to intensify the cutting effect of the beam and to minimize the possibility of perforation of the vessel walls.

Another object of the invention is to provide a flexible catheter adapted to be inserted into a body lumen and having a plurality of laser fibers disposed within the catheter, such fibers being selectively scanned with laser energy by an optical scanner to "aim" the laser energy at a particular target area in the overall cross-sectional area of the body lumen.

Briefly described, the aforementioned objects of the invention are accomplished according to its apparatus aspects by providing a flexible catheter having an outside diameter from about 1.2 to about 5.0 millimeters, which is especially suitable for use in coronary, cerebral and somewhat larger carotid blood vessels, for example, to remove occlusions, such as atheromatous placque. Within the catheter sheath there are provided a plurality of optical fibers and fluid channels.

In one embodiment of the invention, the optical fibers include a bundle of laser transmitting fibers eccentrically arranged relative to the catheter axis and radially movable toward that axis by means of a balloon positioned within the catheter sheath. Each laser fiber has a distal lens system which converges and cants the radiation beam away from the circumference of the catheter and toward the axis thereof. Alternate embodiments of the catheter include distal lens systems for the laser fibers which may comprise one or more diverging lenses for special applications or techniques to be hereinafter described.

A flexible optical fiber viewing element with a distal lens system is provided within the catheter sheath which comprises a plurality of individual fibers having a glass cladding and extending over a substantial part of the cross-sectional area of the catheter, for instance, 50% or more. An illuminating system comprising several individual plastic clad quartz glass fibers cooperates with the optical viewing element and is arranged adjacent thereto for delivering white light from a conventional light source.

Fluid systems within the catheter include an outflow or suction channel for removal of fluids and debris and two or more inflow channels for injection of saline, pharmacologic agents, radiopaque positioning dyes, immuno-specific antibodies and the like. Carbon dioxide gas channels are also provided for inflation/deflation of both the laser aiming balloon and a balloon circumferentially disposed about the catheter adjacent the distal end thereof for occluding the vascular lumen and for establishing stabilization of the catheter distal end relative to said lumen.

A laser microsurgical system is operatively connected to the proximal end of the flexible angiographic catheter and comprises a proximal optical and fluid coupler for interconnecting the optical fibers and fluid channels of the catheter to the various system components, such as the laser apparatus and control, laser fiber optical scanner, illumination and visualization systems, positioning systems and fluid systems.

The objects of the invention are accomplished according to its method aspects by the use of visible light laser energy in the wavelength range of 351 to 515 nanometers, and, preferably, the blue-green emission lines at wavelengths of 488 and 514 nanometers from an argon-ion laser with a peak power output of about 20 watts, such as a Spectra-Physics 171 Laser. The argon laser apparatus is operated in the pulsed or non-conducting mode using a pulse width or duration in the range of from 5 to 200 milliseconds and a pulse repetition rate of 1 to 50 pulses per second with a duty cycle of between 5 and 50%. The preferred pulse energy is in the range of from 150 to 500 millijoules. Spot size for each fiber in the laser fiber bundle may be from 100 to 500 microns, preferably, the largest possible spot size in that range compatible with energy density requirements.

The above parameters of the pulsed laser energy are selected to effect damage to a luminal obstruction with substantially no thermal necrosis of the surrounding tissue. A hole is drilled in the obstruction by heating a given volume of the tissue thereof to its boiling point and then supplying the heat of vaporization to that volume to convert it to vapor. Ideally, the total laser energy needed to vaporize the given volume of the tissue of the obstruction is delivered in such a short period of time that heat conduction to the surrounding tissue is negligible. That time period is defined as the "thermal time constant" or "thermal relaxation time" for the given volume of tissue. According to the invention, the pulse characteristics, e.g., pulse width, pulse repetition rate and energy, are selected to operate in the conduction-free mode, that is, the laser energy is preferably delivered just at the threshold of the thermal relaxation time of the illuminated volume of the obstruction tissue.

Experimental results have indicated that over the range of laser focal diameters of 50 to 100 microns for an argon-ion laser, the diameter of the laser drilled hole in arterial placque is approximately 500 microns, i.e., 5 to 10 times greater than the laser focal diameter. That phenomenon is believed to be the result of a combination of strong, small angle scattering and weak absorption of the placque tissue. The larger area, and consequent larger volume, of illuminated tissue results in a greater energy threshold for drilling the placque, that is, a greater thermal input is necessary because of the scattering of the laser light and the absorption characteristics of the placque. For the argon-ion laser, the energy threshold is about 200 millijoules per pulse over a pulse width of 200 milliseconds or less.

An alternate embodiment of the invention takes advantage of the foregoing experimental results by locating a plurality of laser fibers in a flexible catheter in an array with the laser fibers appropriately spaced to provide substantially complete coverage of the cross-sectional area of a body lumen or vessel with little or no overlapping of the drilled laser hole. Thus, "aiming" may be accomplished by optically scanning the plurality of laser fibers to impinge laser energy on selected target areas, e.g., a plurality of target areas, each having a 500 micron diameter, over the entire crosssectional area confronting the distal end of the catheter. Optical scanning of the laser fibers in a predetermined sequence also permits a greater number of pulses or "shots" to be made in a given time period without exceeding the energy threshold and causing thermal necrosis of the surrounding tissue. The laser fibers disposed adjacent the outermost periphery of the catheter may also be "skewed" toward the center of the catheter to minimize the possibility of perforation of the luminal wall.

With the foregoing and other objects, advantages and features of the invention that will become hereinafter apparent, the nature of the invention may be more clearly understood by reference to the following detailed description of the invention, the appended claims, and to the several views illustrated in the attached drawings.

DETAILED DESCRIPTION OF A PREFERRED EMBODIMENT

Figure 1:
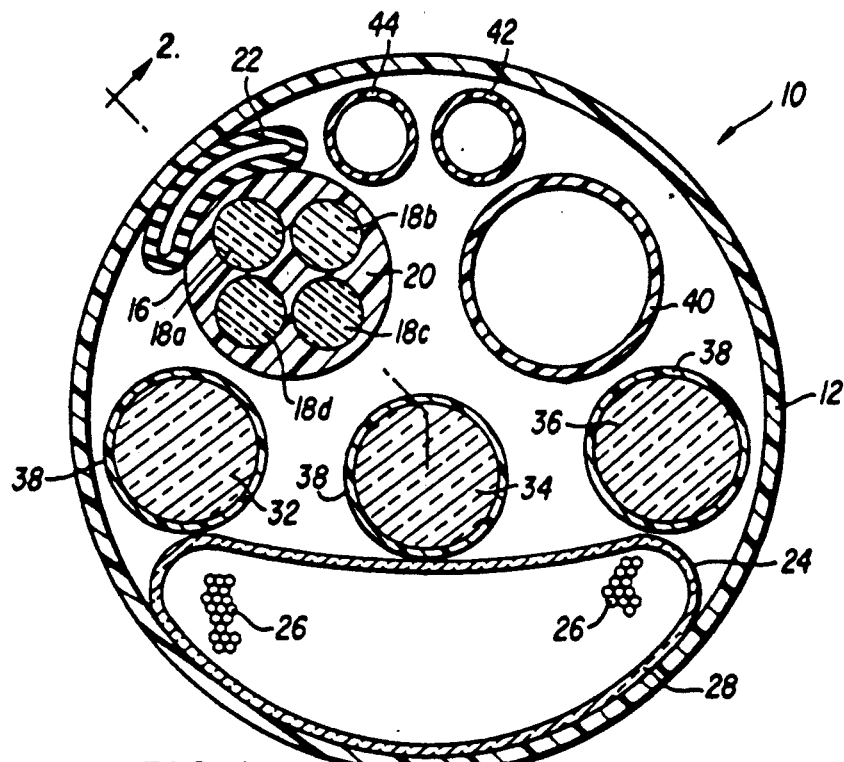
FIG. 1 is a transverse cross-sectional view of a first embodiment of the flexible catheter of the present invention taken along line 1—1 of FIG. 2.
Figure 2:
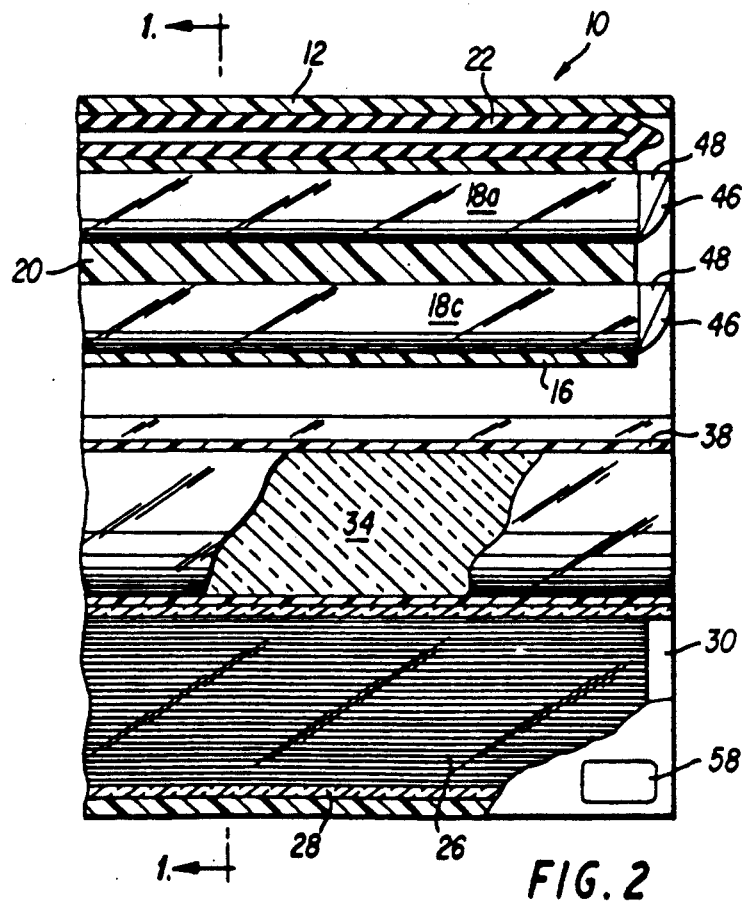
FIG. 2. is a longitudinal cross-sectional view, partly broken, of the first embodiment of the catheter of the invention taken along line 2—2 of FIG. 1.

Referring now in detail to the drawings wherein the same parts are designated by the same reference numerals throughout, there is illustrated in FIGS. 1 and 2 cross-sectional details of the distal end of the inventive flexible catheter which is designated generally by reference numeral 10. In those circumstances wherein a particular element or aspect of the invention has been described in greater detail in one or more of the aforementioned copending related applications, appropriate reference will be made herein to such application(s).

The catheter 10 comprises a plastic sheath 12 which may be a non-toxic polyvinylchloride (PVC) or other suitable non-toxic plastic material. The outside diameter of the catheter 10 for use in the laser coronary angioplasty techniques described herein is from about 1.2 to about 5.0 millimeters, but may be larger in diameter for use in other, larger body lumens.

Disposed within the catheter sheath about the central axis 14 thereof are a plurality of elements extending longitudinally of the catheter and, for convenience of illustration, are shown in FIGS. 1 and 3A-3D as being somewhat loosely disposed in spaced relation to one another. In the actual construction of the catheter, the elements are in closer proximity to one another than shown in the drawings to provide a somewhat greater packing density consistent with the requirement for shifting the laser fiber bundle relative to the catheter axis in the manner described hereinafter.

A laser fiber bundle 16 is arranged eccentrically of the catheter axis 14 and, in a preferred form, comprises four quartz glass laser fibers 18a-18d for transmitting the laser energy, each fiber having a core diameter of from 50 to 200 microns. Laser fibers 18a-18d are embedded in a laminated sheath or cladding 20 of nontoxic polyethylene or PVC. As shown in FIG. 1, the four laser fibers are preferably orthogonally arranged with the axes of two of the fibers 18a and 18c disposed on a radial plane through the catheter axis 14.

An elongate balloon 22 is bonded or otherwise affixed to the circumference of the laser fiber bundle 16 at the portion thereof proximate the catheter sheath 12 and extends parallel to the axis of the laser fiber bundle as shown in FIG. 2. Inflation of the balloon 22 exerts a radially inward force on the laser bundle 16 tending to urge the same toward the catheter axis 14 and thereby "aiming" the laser energy as more fully described hereinafter in connection with FIGS. 3A-3D.

Arranged at the lowermost portion of the catheter, as viewed in FIG. 1, is a visualization optical element 24 which is of generally conventional construction. Optical viewing element 24 is generally crescent-shaped in cross-section and comprises a plurality of 5,000 to 10,000 individual glass fibers 26, each having a hexagonal cross-section to improve the packing factor. The fibers 26 each have a flat-to-flat dimension of about 4 microns and are packed tightly together and fused only at their proximal and distal ends to preserve flexibility. The bundle of fibers is ensheathed in a glass cladding 28 and a lens system 30 (FIG. 2) of known configuration, i.e., two plano-convex lenses, is fused to the distal end of the viewing element 24 for providing wide angle visualization within the body lumen. See also related application Ser. No. 329,978.

Illumination of the surgical area is provided by three fused quartz glass fibers 32, 34, 36 of about 50 microns diameter which are clad with a PVC sheath 38. As shown in FIG. 1, the illuminating fibers are preferably arranged substantially diametrically for most effective illumination of the central portion of the body lumen.

The fluid systems of the catheter, in addition to the laser fiber aiming balloon 22, include a suction channel 40 and two inflow channels 42, 44. The suction channel 40 is used for debris removal and for suctioning fluids from the intraluminal region at the distal end of the catheter. Inflow channels 42, 44 are employed for injecting fluids such as saline, pharmacologic agents, radiopaque positioning dyes and immuno-specific antibodies, among others.

Figure 4:
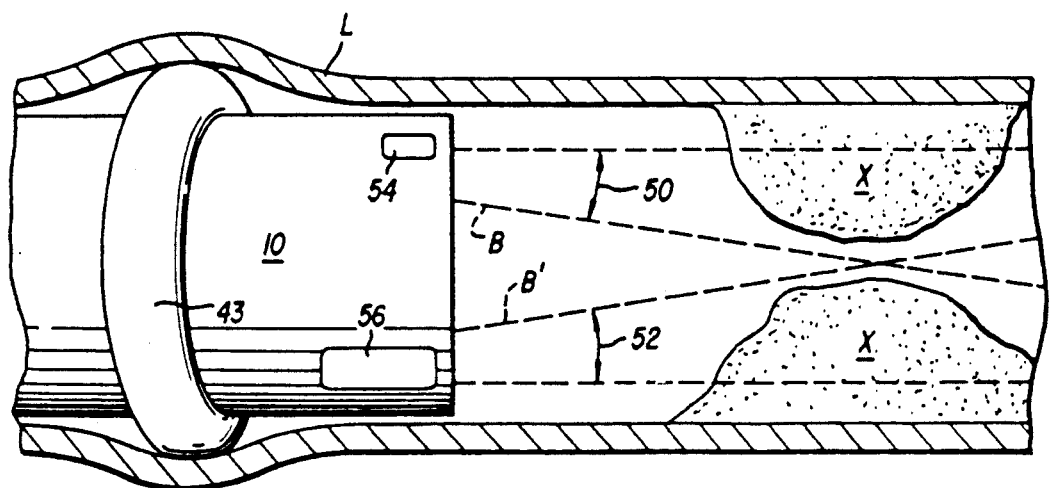
FIG. 4 is a view illustrating the positioning of the distal end of the catheter in a body lumen adjacent a partial occlusion of the lumen.

A conventional circumferential balloon 43 is arranged about the catheter 10 adjacent the distal end thereof as shown in FIG. 4. Inflation of balloon 43 occludes flow in the lumen L and establishes a fixed, stabilized position of the distal end of the catheter 10. Such balloons and the methods and apparatus for inflating and deflating the same are well-known in the art and, therefore, need not be described in greater detail herein.

As shown in FIG. 2, at the distal end of each laser fiber 18a-18d, there is epoxied a converging lens 46 for focusing the laser energy beam and preventing undesirable divergence toward the luminal wall and a prism 48 for bending or "canting" the eccentric laser beam from each fiber toward the center of the lumen. Total divergence angle of the preferred 100-500 micron diameter spot for each fiber is preferably no greater than 5°. Preferably, the optical axes of the prismatically canted laser beams are maintained in parallel relationship to prevent spot "overlap" and beam divergence.

In certain circumstances, it may be desirable to insert a catheter with a laser fiber bundle having a diverging lens system at the end of each laser fiber. For instance, if the distal end of the catheter directly abuts an occlusion of atheromatous placque, a greater laser impact area could be achieved with a diverging lens arrangement. After destruction of the first few millimeters of the placque is accomplished, the catheter would normally be replaced by a catheter having the converging lens system shown in FIG. 2.

Figure 3A:
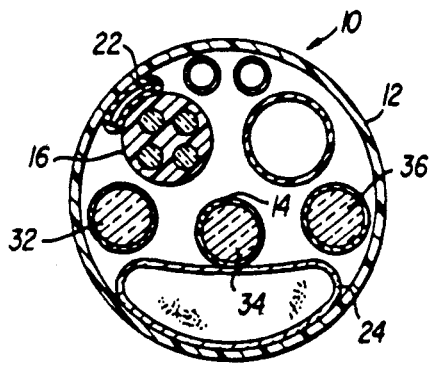
FIGS. 3A–3D are transverse cross-sectional views similar to FIG. 1 showing the positioning of the laser fiber bundle.
Figure 3B:
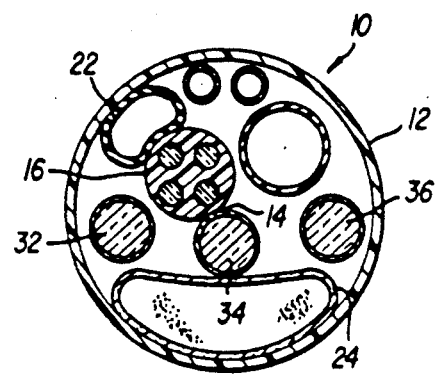

With reference now to FIGS. 3A-3D, FIG. 3A corresponds substantially to FIG. 1 and shows the balloon 22 in its deflated condition with the laser fiber bundle in its most eccentric radial position in relation to the central axis 14 of the catheter. As the balloon 22 is gradually inflated, the laser fiber bundle is incrementally urged substantially radially toward the axis 14 until it reaches a position of minimum eccentricity as shown in FIG. 3B.

Figure 3C:
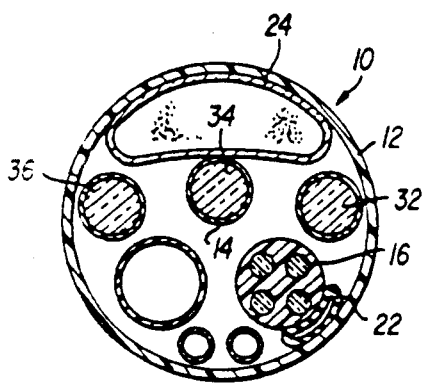
Figure 3D:
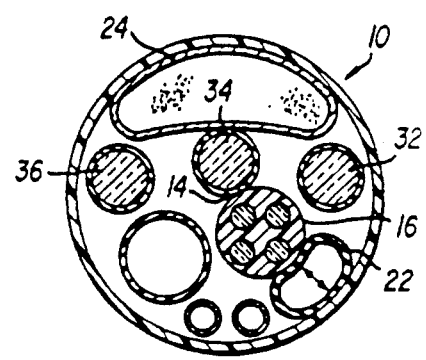

FIGS. 3C and 3D illustrate the same conditions of inflation/deflation of balloon 22 as shown in FIGS. 3A and 3B, respectively, except that the catheter 10 has been rotated exactly 180°. It will be understood by those skilled in the art that by the appropriate selection of angle of rotation of the catheter and incremental inflation/deflation of balloon 22, the four 200 micron spots from the laser fibers 18a-18d can be positioned to impinge at any target area over virtually the entire cross-sectional area of the body lumen being treated.

Referring now to FIG. 4, the distal end of the catheter 10 is shown fixed in position in a lumen L adjacent a partial occlusion X. The uppermost pair of diverging dotted lines represents a laser energy beam B from laser fiber 18a when said fiber is positioned on a vertical plane at a location of greatest eccentricity from the catheter axis. Beam B has a total divergence angle 50 of 5°; however, because the beam has been prismatically canted by the lens system 46, 48 shown in FIG. 2, the diverging beam does not impinge on the wall of the lumen L, but rather is directed toward the central portion of the lumen L. Likewise, the lowermost pair of diverging dotted lines in FIG. 4 represents a laser energy beam B' from laser fiber 18a when said fiber is positioned exactly 180° from the position at which beam B was generated. Beam B' also has a total divergence angle 52 of 5° as shown in FIG. 4.

It should be apparent from the foregoing description of FIGS. 3A-3D and FIG. 4 that the laser energy beams transmitted by the laser fiber bundle 16 of the catheter are not only capable of being "aimed" at virtually any target area within the lumen, but are converged and canted so as to minimize the possibility of laser beam impingement on the lumen walls.

Positioning of the distal end of the catheter 10 is aided by known radiographic visualization procedures. For this purpose, it is advantageous to mark the periphery of the distal end of the catheter with a plurality of radiopaque strips 54, 56, 58 of predetermined size and positioned for determining both the rotational and axial positions of the catheter within a coronary artery, for example.

Figure 5:
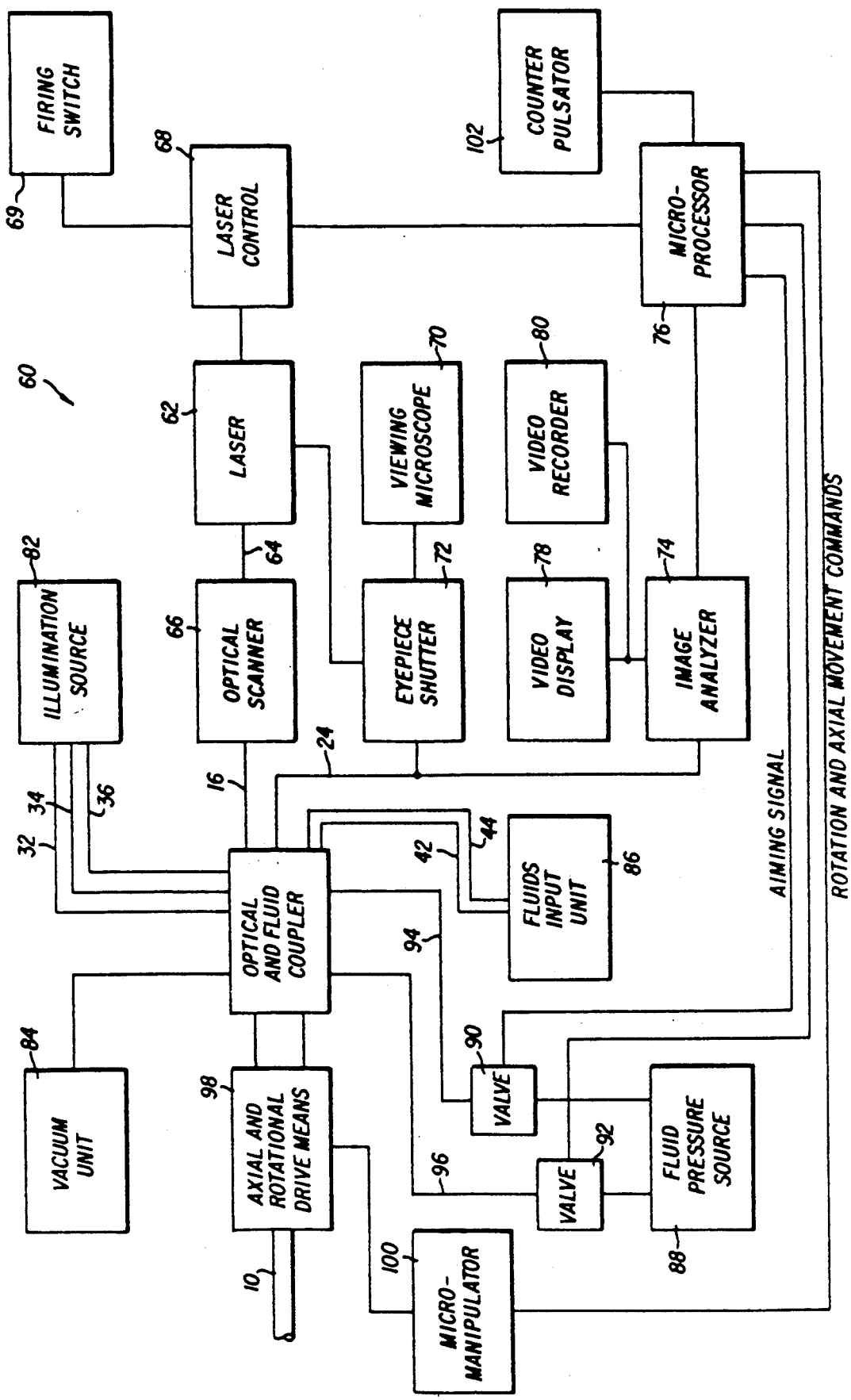
FIG. 5 is a schematic block diagram showing the laser microsurgical system of the present invention.

The laser microsurgical system 60 of the invention is shown schematically in FIG. 5. The system 60 includes a laser source 62 which is preferably an argon-ion laser, such as a Spectra-Physics 171 Laser for generating a pulsed laser beam. The output of laser source 62 is a pulsed laser beam 64 which is inputted to a multi-fiber optical scanner 66 of a known type, for example, of the type described by Fujii et al in Applied Optics, Vol. 21, No. 19, pp. 3437-3442, Oct. 1, 1982. Scanner 66 is used to scan the four laser fibers 18a-18d of the laser fiber bundle 16 with pulsed laser beam 64.

Control of pulse width or duration, pulse repetition rate, wavelength, length of exposure, intensity and firing is provided by a laser control 68 associated with the laser source 62. Firing of the laser 62 is accomplished by closing a firing switch 69 which may be, for example, a foot pedal switch.

The proximal end of the optical visualization element 24 supplies an optical image to a viewing microscope 70 which has a built-in eyepiece shutter mechanism 72. The shutter 72 is responsive to activation of the laser source 62 to prevent back-scatter of laser energy which could damage the surgeon's eyes.

The optical image from optical element 24 is also supplied to an image analyzer 74 controlled by microprocessor 76 both of which are used to analyze the visual images transmitted from the intraluminal region at the distal end of the catheter and to aid in longitudinal positioning of the catheter distal end, "aiming" of the laser fiber or fibers at the appropriate target in the intraluminal region and timing of the laser firing signal in relation to the cardiac cycle. A suitable microprocessor and image analyzer is a Videoplan Computerized Image Analyzer available from Carl Zeiss, Inc., 444 Fifth Avenue, New York, N.Y. 10018.

A conventional cathode ray tube video display 78 and video recorder 80 are connected to the image analyzer for real time observation and recording, if desired, of the microsurgical procedure.

An illumination source 82 is connected to the proximal ends of optical fibers 32, 34, 36 for delivery of white light thereto. The light is provided by mercury or xenon high pressure arc lamps within quartz enclosures; however, other types of light sources may be used. A vacuum unit 84 and fluids input unit 86 are connected to the suction channel 40 and fluid inflow lines 42, 44, respectively.

For inflation and deflation of the aiming balloon 22 and circumferential balloon 43, a fluid pressure source 88, such as pressurized carbon dioxide, is connected through respective electrically-operable solenoid valves 90, 92 to the pneumatic tubes 94, 96 supplying the aiming balloon 22 and the circumferential balloon 43, respectively.

The proximal end of the catheter 10 is mounted in an axial and rotational drive mechanism 98 which rotates the catheter about its axis and moves the same axially in response to mechanical or electrical signals from a micromanipulator 100 which, in turn, receives command signals from the microprocessor 76. Suitable micropositioners are well-known in the art and are available from numerous sources, such as Klinger Scientific Corporation, 110-120 Jamaica Avenue, Richmond Hill, N.Y. 11148. See also related application Ser. No. 329,978.

It is also advantageous to synchronize the occlusion of the coronary artery with the balloon 43 and the firing of the laser 62 with the cardiac cycle. Generally, it is desirable to inflate the catheter balloon 43 during the filling phase of the cardiac cycle and deflate the balloon during the pumping phase of the cardiac cycle. In that way, blood flow is occluded under minimal pressure conditions in the coronary artery. For this purpose, a conventional counterpulsator 102 may be used which senses ventricular output with an aortic catheter independently of the catheter 10 of the invention. One suitable counterpulsator is known as System 82 and is manufactured by Datascope Corporation, 580 Winters Avenue, Paramus, N.J. 07652. See also related application Ser. No. 329,978.

Figure 6:
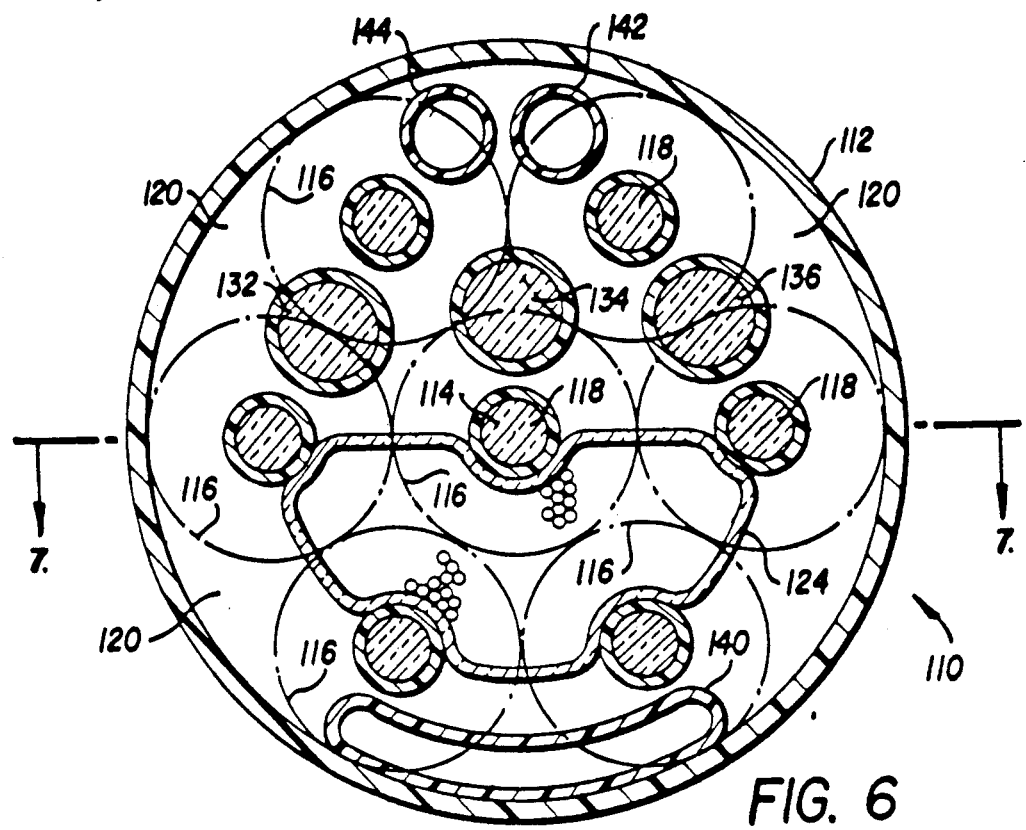
FIG. 6 is a transverse cross-sectional view of the distal end of an alternate embodiment of the flexible catheter of the present invention, taken along line 7—7 of FIG. 6.

An alternative or second embodiment of the catheter of the invention is shown in FIG. 6 and identified with reference numeral 110. The catheter 110 comprises a plastic sheath 112 similar to the sheath 12 of the FIG. 1 or first embodiment of the invention, the outside diameter of which is preferably from about 1.2 to about 5.0 millimeters for use in the described laser coronary angioplasty techniques. The FIG. 6 embodiment illustrates a catheter having an outside diameter of about 1.5 millimeters which diameter is essentially defined by the arrangement of the laser fiber array disposed within the sheath 112 as explained in greater detail hereinafter.

A plurality of elements similar to those illustrated in FIGS. 1 and 2 are arranged to extend longitudinally within the sheath 112 about the longitudinal axis 114 thereof and, like the showing of FIG. 1, are somewhat loosely disposed in relation to one another, although in actual practice the elements are packed in closer proximity, preferably in a fixed relationship to one another and to the sheath 112.

The catheter 110 has a similar arrangement of optical viewing element 124, illumination fibers 132, 134, 136, suction channel 140 and inflow channels 142, 144 as the first embodiment of the invention. However, in contrast to the laser fiber bundle 16 of the first embodiment of the invention, individually clad laser fibers 118 of the second embodiment are disposed about the catheter axis 114 in a predetermined, parallel array designed to provide impingement of laser energy on substantially the entire cross-sectional area of an obstruction confronted by the catheter 110 with little or no overlapping of laser impingement.

Inasmuch as experiments have indicated that drilled holes with an argon-ion laser have a diameter of about 500 microns regardless of laser focal diameter, an array of seven (7) 50 to 200 micron diameter fibers 118 in the arrangement shown in FIG. 6 will provide laser energy coverage of virtually the entire cross-sectional area of a luminal obstruction confronting the catheter 110, particularly in the central region thereof as shown by the dashed line areas 116 of laser impingement. Advantageously, the largest areas 120 not included in the total laser impingement area are located at the outermost periphery of the catheter adjacent the vessel walls where laser energy impingement is least desirable, and, in fact, may be detrimental.

In view of the above teachings, various arrangements of laser fibers for different diameter catheters will be apparent to those skilled in the art. For example, the same seven (7) fiber array may be used for a 1.2 millimeter diameter catheter by arranging the centers of the laser fibers at a 400 micron spacing rather than the 500 micron spacing shown in FIG. 6. While a certain amount of laser impingement overlap will result from that arrangement, by appropriate scanning of the laser fibers with laser energy any overheating of the tissue can be avoided.

Generally speaking, a laser fiber disposed on the axis 114 of the catheter is preferred, but is not essential. Thus, although a 1.2 millimeter diameter catheter is preferably provided with an array of 5 to 7 laser fibers, an array of four (4) laser fibers equiangularly spaced may be provided with their impingement areas in tangential relationship. While such an arrangement would not provide laser impingement in the central region of an obstruction confronting the catheter, destruction of the obstruction surrounding the central region will eliminate support of such central region and ultimately cause it to gravitate to a laser impingement area where it will be destroyed.

In larger diameter catheters, a larger number of laser fibers are preferably employed. For instance, a 5.0 millimeter diameter catheter encompasses an area 100 times greater than the 500 micron diameter area impinged by a single laser fiber. Therefore, an array of 80 to 100 laser fibers would be required to cover the entire area confronted by a 5.0 millimeter diameter catheter.

The laser microsurgical system 60 shown schematically in FIG. 5 may also be used with the second embodiment of the catheter 110 of the invention shown in FIG. 6. Advantageously, the multi-fiber optical scanner 66 may be programmed to scan each of the laser fibers 118 with pulsed laser energy in a preselected sequence. The scanning sequence is preferably selected to operate in the conduction-free or non-heat conducting mode. In that way, the possibility of overheating and the consequent thermal necrosis of a given impingement area is avoided, while at the same time the number of pulses of laser energy that can be delivered to the impingement area in a given time period is maximized.

Figure 7:
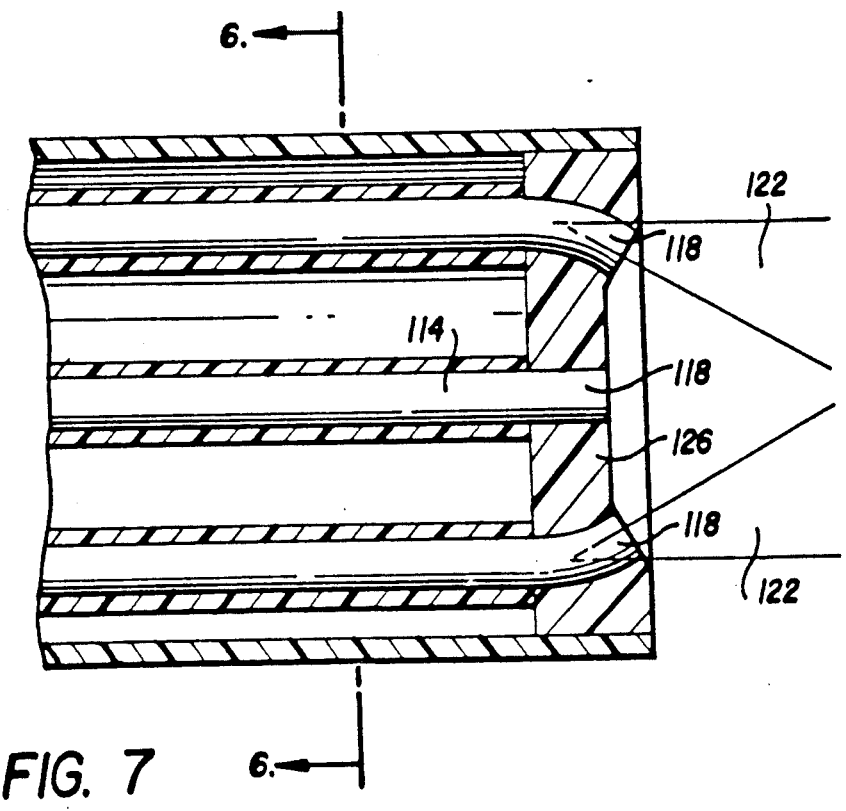
FIG. 7 is a longitudinal cross-sectional view of the catheter of FIG. 6 taken along line 7—7 showing skewing of the outermost laser fibers.

Although the laser fibers 118 of the second embodiment of the invention are described above as extending parallel to the catheter axis 114, as shown in FIG. 7, the distal ends of the outermost laser fibers may also be inclined or skewed inwardly toward the catheter axis by an angular amount identified by reference numeral 122. The amount of skewing may amount to between 5° and 45°. Preferably, the distal ends of the laser fibers 118 are inserted or molded into an end plate 126 fixed to the sheath 112. The end plate 126 may also receive the other longitudinally extending elements of the catheter, such as the viewing element 124, illumination fibers 132, 134, 136 and fluid channels 140, 142, 144.

The above-described skewing of the peripheral laser fibers advantageously causes the outermost laser energy beams to converge toward the axis of the body lumen or vessel and thereby provide further protection against the possibility of perforation of the luminal wall. Such skewing, however, reduces the total area of laser illumination of a given diameter of catheter and arrangement of laser fibers and results in varying degrees of laser beam overlap depending on the distance between the obstruction and the distal end of the catheter.

It would be possible to skew the distal ends of some of the interiorly disposed laser fibers of an array having fiber groups disposed at varying radial distances from the axis of the catheter. Such skewing may cause the axes of the fibers to diverge or converge with the catheter axis so as to achieve overlapping of laser impingement if desired or to "aim" at areas not impinged by the laser beam or blind spots caused by the positioning of other elements in the catheter, such as the elements 124, 132, 134, 136, 142, 144, etc.

According to the method of the present invention, laser energy is not supplied as continuous wave (CW) laser energy in the thermal mode to vaporize atheromatous occlusions as in the prior art, but rather as pulses of 5-200 millisecond duration at a pulse repetition rate of 1-50 pulses per second and a duty cycle of between 5 and 50%. The pulse energy is from 150 to 500 millijoules. The laser source 62 is an argon-ion laser delivering 20 watts peak power at wavelengths of about 488 and 514 nanometers and a preferred spot size of about 100-500 microns diameter. Pulsing of the laser source in the ranges described above has been advantageously found to be both safe and effective; safe from the standpoint that the vessel walls will neither be perforated nor subjected to thermal necrosis, and effective from the standpoint that the laser energy is sufficiently great to effect vaporization of the occlusion.

The selection of specific values for the pulse duration, pulse repetition rate, pulse energy parameters within the aforesaid ranges to effect destruction of an occlusion without thermal necrosis is dependent to a large extent on the thermal time constant and absorption characteristics of particular type or material of the occlusion, e.g., fibrin, cholesterol, calcium, collagen, low-density lipoproteins and the like. Based on the teachings herein, however, one skilled in the art can readily select a suitable value for each pulse parameter to effect conduction-free operation, i.e., destruction of the tissue of the occlusion with substantially no thermal necrosis of the surrounding tissue.

Although only preferred embodiments are specifically illustrated and described herein, it will be appreciated that many modifications and variations of the present invention are possible in light of the above teachings and within the purview of the appended claims without departing from the spirit and intended scope of the invention.

What we claim is:

1. A method of performing laser angioplasty by effecting damage to an obstruction in the vascular system of a human comprising:
   generating a non-continuous wave, pulsed laser beam having a predetermined pulse duration, pulse repetition rate, pulse energy and duty cycle selected to operate substantially at the threshold of the thermal relaxation time of the irradiated volume of the obstruction such that damage is effected to the obstruction with substantially no thermal necrosis of the surrounding tissue of the vascular system;
   inserting a flexible optical fiber into the vascular system of a human; and
   transmitting said laser beam through said flexible optical fiber to the obstruction in the vascular system.

2. A method of performing intraluminal laser surgery in a human body having a tubular lumen occluded or partly occluded by an obstruction comprising the steps of:

providing at least one flexible optical fiber having a diameter smaller than the diameter of the tubular lumen, said fiber having proximal and distal ends;

inserting said flexible optical fiber into said tubular lumen such that the distal end of the fiber is positioned adjacent the obstruction in the lumen and the proximal end of the fiber is out of the lumen;

generating a non-continuous wave, pulsed laser beam having a pulse duration, pulse energy and pulse repetition rate;

irradiating the proximal end of the fiber with said pulsed laser beam to thereby transmit the pulsed laser beam from the proximal end of the fiber to the distal end of the fiber; and controlling the pulse duration, pulse energy and pulse repetition rate of the pulsed laser beam so that the pulsed laser beam impinges upon and vaporizes the material of the obstruction with substantially no thermal necrosis of the surrounding lumen tissue.

3. The method of claim 2, including step of inserting a flexible tubular duct into said tubular lumen with said flexible optical fiber for introducing fluids into the lumen or exhausting fluids from the lumen.

4. The method of claim 2, including the step of impinging the laser beam selectively on different areas of the obstruction.

5. The method of claim 4, wherein said at least one fiber comprises a plurality of said fibers and including the step of optically scanning the proximal ends of said fibers with said pulsed laser beam.

6. The method of claim 2, wherein said laser surgery is laser angioplasty.

* * * * *